United States Patent [19]
Becker

[11] Patent Number: 5,260,574
[45] Date of Patent: Nov. 9, 1993

[54] INFRARED DENSITOMETER

[75] Inventor: Roger J. Becker, Kettering, Ohio

[73] Assignee: The United States of America as represented by the Secretary of the Air Force, Wright-Patterson Air Force Base, Ohio

[21] Appl. No.: 904,627

[22] Filed: Jun. 26, 1992

[51] Int. Cl.$^5$ .................................. G01N 21/59
[52] U.S. Cl. .................. 250/338.1; 250/339; 250/345; 356/319; 356/321; 356/323; 356/325
[58] Field of Search ............ 250/338.1, 345, 339; 356/325, 323, 321, 319

[56] References Cited

U.S. PATENT DOCUMENTS

| | | | |
|---|---|---|---|
| 3,062,088 | 11/1962 | Bolz | 356/321 |
| 4,553,033 | 11/1985 | Hubble, III et al. | 250/353 |
| 4,796,065 | 1/1989 | Kanbayashi | 355/14 E |
| 4,937,637 | 6/1990 | Magistro | 356/73 |
| 4,989,985 | 2/1991 | Hubble, III et al. | 356/445 |

OTHER PUBLICATIONS

"Dual Beam Recording U.V.-Visible Ultra-Microspectrophotometer and Scanning Microdensitometer," Pamphlet from Canalco, Canal Industrial Corporation of Bethesda, Md., 4 pages. Undated, but prior to receipt in Office on Oct. 15, 1962.

Primary Examiner—Constantine Hannaher
Attorney, Agent, or Firm—Bobby D. Scearce; Thomas L. Kundert

[57] ABSTRACT

A high resolution infrared densitometer system is described which comprises an intense thermal light source, an optical system for projecting first and second images of the light source along respective parallel first sample and second reference optical axes, adjustable optical attenuators for selectively balancing the light intensity of the images projected along the sample and reference axes at selected optical density, a spectrometer for filtering background radiation from the projected images except for a selected wavelength, and a detector for measuring intensities of the filtered projected images. A method for making optical density measurements is described.

21 Claims, 2 Drawing Sheets

INFRARED DENSITOMETER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to instruments for measuring transmission of optical components, and more particularly to a high resolution infrared (IR) densitometer for measuring optical densities up to about 6 in the 1-5 micron ($\mu$) spectral range.

The densitometer described herein meets the extremely exacting need for measurement of optical attenuation across a narrow band of an IR signal within the 1-5 $\mu$ wavelength range. The invention has a specific application in the characterization of high density rejection line filters, for which a high resolution system is required. Attenuation levels encountered in such an application greatly exceed measurement capabilities of conventional equipment (typically limited to densities of 3-4 over a 2-3% bandwidth). Measurement of a large attenuation factor requires a system with a correspondingly high signal-to-noise ratio. Thus to measure a density of 6, the optical power to be delivered to the detector must be $10^6$ times the noise level of the detector; the light source must have high power output and the detector must have a low noise level. Since the system must operate at any wavelength across a broadband, both light source and detector must be broadband (in contrast to conventional equipment which operate on fixed wavelengths), and the system should be capable of characterizing notch filters.

The only practical light source continuously covering the 1-3 $\mu$ region is an incandescent source, or hot filament. A thermal source of this type, while providing requisite power across the band, operates only with simultaneous output at all wavelengths. The broadband detector responds to each of these wavelengths. The intense broadband radiation at wavelengths other than the very narrow one at which a measurement is made must be removed or it will contribute a noise signal which swamps the measurement. Typically, the stray light needs to be reduced by a factor of about $10^9$ while the signal at a selected wavelength is preserved, which calls for a passband filter to be placed in series with the stop band notch filters. Thus the system filter must have a continuously tunable passband wavelength and must reject stray light by a factor of about $10^9$. A useful filter means for the system is a high-performance grating spectrometer. The densitometer of the invention therefore comprises three basic components, viz, an intense thermal light source, a low-noise broadband detector and a spectrometer for stray light rejection.

It is therefore a principal object of the invention to provide an improved densitometer.

It is a further object of the invention to provide a high resolution infrared densitometer for measuring optical densities to about 6 in the 1-5 $\mu$ spectral range.

It is another object of the invention to provide an infrared densitometer for measuring optical densities of high density optical filters.

These and other objects of the invention will become apparent as a detailed description of representative embodiments proceeds.

SUMMARY OF THE INVENTION

In accordance with the foregoing principles and objects of the invention, a high resolution infrared densitometer system is described which comprises an intense thermal light source, an optical system for projecting first and second images of the light source along respective parallel first sample and second reference optical axes, adjustable optical attenuators for selectively balancing the light intensity of the images projected along the sample and reference axes at selected optical density, a spectrometer for filtering background radiation from the projected images except for a selected wavelength, and a detector for measuring intensities of the filtered projected images.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
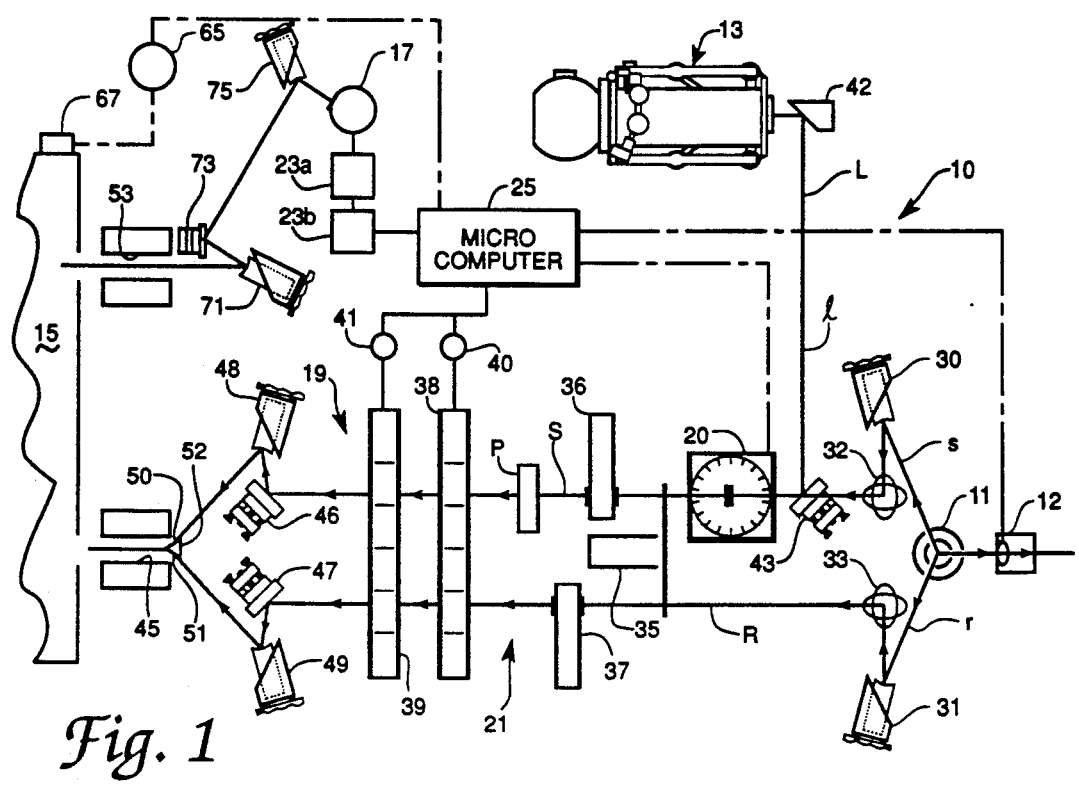
FIG. 1 is a schematic layout of the essential components of an infrared densitometer representative of the invention.

Referring now to the drawings, FIG. 1 is a schematic layout of the essential components of infrared (IR) densitometer 10 representative of the invention. Densitometer 10 includes a pair of light sources 11,13, spectrometer 15, photodiode detector 17, sample optics 19 and reference optics 21 disposed along respective closely-spaced parallel optical axes S,R, and associated signal processing electronics 23 and microcomputer 25.

Light source 11 provides reference and sample beams r,s projected along respective closely-spaced optical axes R,S. Source 11 is preferably a thermal source of broad spectral character to provide desired flexible wavelength capability to densitometer 10; for example, arc lamps have undesirably small effective surface area and standard incandescent lamps have long wavelength cutoffs and low IR emissivities that would limit operation in the IR. Source 11 may, as in an embodiment built in demonstration of the invention, comprise a Nernst hot filament source, mounted on an x-y translation stage, having a SiC filament of 10 mm$^2$ effective surface area and 0.9 emissivity, and presenting a spectral output from about 0.3 $\mu$ in the ultraviolet (UV) to about 10 $\mu$ in the IR; maximum output power desirable for measuring large optical densities may be obtained near 1.5 $\mu$ by running the filament above 2300° K. with good power supply and control circuit stability (~0.2%), which temperature is more than 200° K. above the design operating temperature. High temperature operation shortens (to $\leq 100$ hr) operating life of the filament, but increases output power, especially at 1-1.5 $\mu$. Drive electronics 12 for source 11 may include a one-kHz reversing polarity and DC power supply with feedback control to maintain filament temperature, operatively connected to and controlled by computer 25.

According to a principal feature of the invention, light from source 11 is projected by separate beams r,s through matched reference and sample optics 19,21 and sample 20. In matched optics, the luminosity (equals the product of beam area and solid angle at any point along the optical path) does not increase along the optical train. The filament of source 11 must be mounted vertically in order to prevent sagging at high temperature, and, if spectrometer 15 has horizontal entrance slits (as in the demonstration unit) a pair of flat mirrors 30,31 may rotate the image of the filament to a desired orientation.

Collection and focusing of light from source 11 into reference and sample beams r,s transmitted along axes R,S is achieved in the demonstration unit using off-axis parabolic mirrors 32,33 rather than spherical mirrors, parabolic mirrors being preferable in order to minimize image blur caused by mirror aberrations and to minimize image size at detector 17. Image preservation along both sample and reference optics 19,21 is therefore substantially improved (~6 dB) without using beamsplitters, lenses or rotating mirrors; chromatic aberration, light absorption and background emission in optics 19,21 are substantially eliminated, signal levels of beams r,s are maximized, system reliability is optimized, and optics 19,21 may therefore be used at substantially any wavelength from the UV to the far IR.

Light chopper 35 is disposed along axes R,S near sample 20 for selectively modulating beams r,s to reduce background, electronic and thermal noise and so that densitometer 10 can be operated substantially immune from drift on long (sec) time scales. Chopper 35 may comprise a rotatable polished aluminum blade disposed along axes R,S near sample 20 as suggested in FIG. 1 to take advantage of the folding of beams r,s provided by mirrors 30,31 so that blade size is minimized; blade surface may be unanodized to exhibit low emissivity to reduce background emission reaching detector 17. Size and space constraints of mounting means for components in optics 19,21 of the demonstration unit established a spacing for axes R,S at about $4\frac{1}{4}$ inches and a blade diameter of about 8 inches. A shroud (not shown) having adjustable ports for passing beams r,s was constructed for chopper 35, and operating frequencies were held below 150 Hz in order to minimize air drag on the rotating blade.

Chopper 35 may be configured and rotated to alternately block beams r,s for long (10-100 sec) time intervals and successive measurements are compared by multiplying measured power levels by corresponding attenuation factors, which measurements are simple to make but may lack desirable precision resulting from drift of beams r,s. Alternatively, the blade may be asymmetric in order to pass beams r,s simultaneously with no signal level modulation when intensity levels of beams r,s are equal, which results in a highly accurate null measurement, the precision of each measurement being sensitive to careful calibration of system optics.

Sample and reference optics 19,21 include respective fixed optical attenuators 36,37 (neutral density filters in the demonstration unit) and variable optical attenuators 38,39 as shown in FIG. 1, each attenuator having essentially flat optical response from about 1 to 9 $\mu$. Attenuators 36,37 in the demonstration unit comprised gold plated $CaF_2$, which can be used at about any wavelength length from about 0.9 to beyond 9 $\mu$, and which exhibit densities ranging from about 0.5 to 3. Other filters (not shown) covering 0.4-2.5 and 2.5-6 $\mu$ ranges and densities to about 4 may also be used. Variable attenuators 38,39 permit null measurements and comprised respective control units 40,41 in the demonstration unit. Each unit 40,41 includes precision, adjustable, wide aperture slits controlled by a wide aperture slit jaw mechanism, 200 step/revolution stepper motor and associated servo-control circuit, and controller and power supply capable of up to 10,000 steps per second, and are operatively connected to and controlled by computer 25. Slit position in each adjustable slit is controlled by two linear variable differential transducers (LVDT) having 0.001% reproduceability over a one-inch travel, and slit position is determined by analog-to-digital conversion performed by computer 25. The slits are suitable for operation at any wavelength from the UV to the far IR and have a dynamic range to 50 dB. Additional fixed attenuators (not shown) may be used with the variable attenuators at densities to about 3 in order to extend the dynamic range of attenuators 38,39 at high optical densities. Further, a polarizing film may be introduced along axis S such as at P in FIG. 1 to permit polarization measurements.

In the operation of densitometer 10, optics 19,21 are balanced so that optical signals represented by beams r,s are equal. Sample 20 is placed as suggested in FIG. 1 along optical axis S and the attenuation of reference optics 21 selectively adjusted utilizing variable attenuator 39 until signals along axes R,S are again balanced. Sample 20 density at the selected wavelength is taken as the increase in density observed along reference axis R. Measurement accuracy depends on the calibration of fixed and variable attenuators 36-39. Fixed attenuators 36,37 are stepped in increments of 5 dB, so in principle, variable attenuators 38,39 need only have a dynamic range of about 10 dB.

To measure the optical density of a sample, a signal versus wavelength sample profile is made, and a blackbody reference profile with the sample out of the densitometer is made concurrently for comparison with the sample profile. First, a survey scan is taken over a broad wavelength region of the sample to locate the low transmission (high density) region. A typical survey scan covers about 0.5 $\mu$ (1-2 $\mu$ for the reference profile) using slit widths of 1.5 mm on spectrometer 15. Successive scans are made, each covering a smaller wavelength region; a typical scan which pinpoints the high density regions of the sample covers about 0.01-0.02 $\mu$. The optical density of a sample is determined by comparing the reference scan made with the sample out to one made with the sample in, at a wavelength where the sample is most dense. Optical density equals log (signal with sample out/signal with sample in).

In taking an optical density measurement at a specific wavelength (null measurement), spectrometer 15 is set at the desired wavelength and source 11 current is adjusted to produce a signal detectable with sample 20 inserted. OPEN positions (without sample 20) are then defined for each variable slit (attenuators 38, 39). The slits may be opened wide to maximize signal strength, but slit width must be restricted to the linear operation region of the LVDTs. Signals along each axis S,R are then measured as references prior to closure of the slits to produce the desired attenuation effects. Beam r,s intensities must then be balanced (equalized), by closing the variable slit of the stronger (beam s) of the two beams, and the LVDT readings for the each slit are recorded. Sample 20 is then disposed along beam s, and beam r is attenuated (using the corresponding variable slit and neutral density filter in beam r) until the two beams are again equal in intensity. The density of sample 20 is then determined as the sum of the known density of the neutral density filter and the density derived from an attenuation calibration curve (density vs LVDT value) for the variable slits.

Maximum optical density measurements may be made using external auxiliary light (laser) source 13 to provide increased power through sample optics 19 in the 3-5 $\mu$ range. Beam l from source 13 may be directed along optical axis L utilizing suitable optics represented in FIG. 1 by flat mirror 42 and directed into sample optics 19 using kinematically mounted mirror 43 without otherwise disturbing or realigning either sample or reference optics 19,21. With injection of beam l into sample optics 19, light directed along reference axis R may continue to originate at (Nernst) source 11. Null measurements may therefore be made in conjunction with use of a laser source 13 in manner as suggested above. In the demonstration unit, a PbS laser diode was used as source 13. A density measurement of 8 or higher may be obtained depending on laser diode and detector selection. Because a laser diode is only about 100 $\mu$ in size, some magnification of the diode image may be desirable and may be provided by using an off-axis mirror as mirror 42 to collect light from the laser. A series of lead-salt diodes may be used to fully span the 3.5-5 $\mu$ range. Light from these other fixed wavelength lasers (not shown) can be introduced simultaneously with beam l utilizing suitable mirrors in optics 19. Utilization of auxiliary light source 13 extends the flexibility of densitometer 10 by greatly increasing its dynamic range. It is noted further that other forms of external light sources may be used as well as lasers, such as external incandescent or arc sources, all without otherwise modifying optics 19,21. A second thermal source may be especially useful for operation in the visible and UV.

Figure 2:
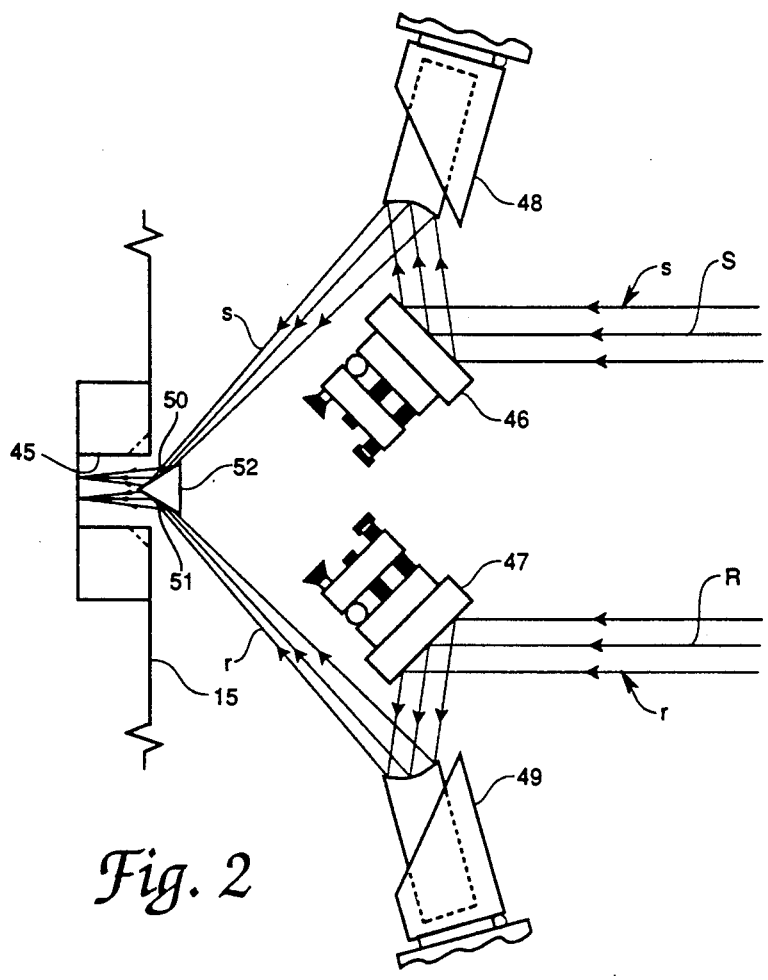
FIG. 2 is an enlarged view of the portion of FIG. 1 depicting the input optics for the spectrometer element of the densitometer.

Elimination of beamsplitters in optics 19,21 eliminates cross talk between beams r,s and requires that beams r,s be adjacent rather than superimposed at spectrometer 15 and detector 17. Beams r,s are therefore separately focused onto entrance slit 45 of spectrometer 15 using a pair of flat mirrors 46,47, a second pair of off-axis (f/7.3) parabolic mirrors 48,49, and a pair of closely spaced flat mirrors 50,51 defined by two gold coated surfaces of a 6 mm precision 60° prism 52. Beam r,s spacing at slit 45 is about 1 cm, which is small compared to both the one meter focal length and 12 cm equivalent diameter of the mirrors within spectrometer 15. The spectrometer input optics arrangement is shown more clearly in the enlarged view of FIG. 2, and was shown to significantly enhance optical throughput (factor of 2) without moving parts.

Spectrometer 15 provides required tunable high-resolution filter means for dispersing (rejecting) stray light in order to accurately measure the intensity of a narrow line subtracted from the spectral continuum provided by source 11. The signal level for the desired measurements in the practice of the invention may be upwards of the order of $10^9$ weaker than background. A double stray light rejection obtainable with a reasonable slit width and solid angle in a single monochromator is about $10^4$. Spectrometer 15 used in demonstration of the invention comprised a one meter Instruments SA model ISA U-1000 double monochromator. Stray light rejection for a monochromator may be approximated by the ratio of the focal length of the optics to the slit width. For n monochromators arranged in series, this factor is raised to the nth power. Because the selected spectrometer 15 functions as a triple monochromator, stray light rejection of $10^9$ with one mm slits is theoretically achievable. Measurements in the visible using a laser indicated stray light rejection greater than $5 \times 10^9$, 0.5% away from the laser wavelength using 400-$\mu$ slits; at a 300-$\mu$ slit width, rejection in second order was $2 \times 10^{10}$ 0.4% away from the laser line. In first order, at 1.6 mm slit width, rejection was about $10^8$ 1% away from center frequency. Spectrometer resolution is also given by the ratio of focal length to slit width, so that stray light rejection may also be increased by increasing resolution. Since throughput decreases as the square of slit width, spectrometer 15 throughput must be balanced with stray light rejection for optimum results.

Figure 3:
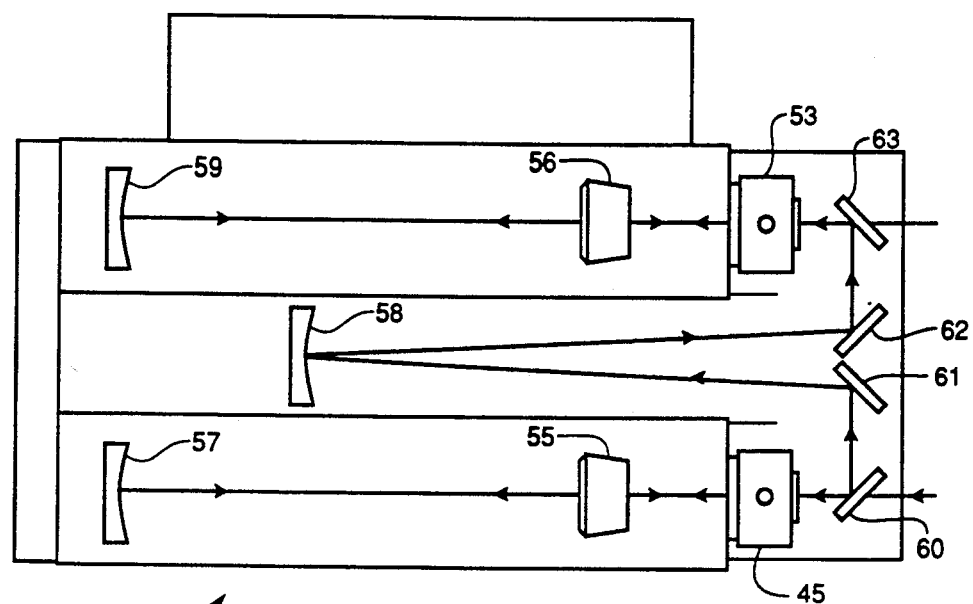
FIG. 3 is a schematic layout of the spectrometer optics of the FIG. 1 densitometer.

FIG. 3 shows schematically the optical layout of spectrometer 15. Spectrometer 15 includes entrance slit 45, exit slit 53, two 10-cm rotatable gratings 55,56, three spherical mirrors 57-59 and four flat mirrors 60-63; all mirrors are preferably gold coated. Alignment of spectrometer 15 optics is critical. Ultimate resolution is about 0.005% at narrow (10 $\mu$) slit widths. Controller 65 for spectrometer 15 was interfaced with computer 25 through serial port 67.

Figure 4:
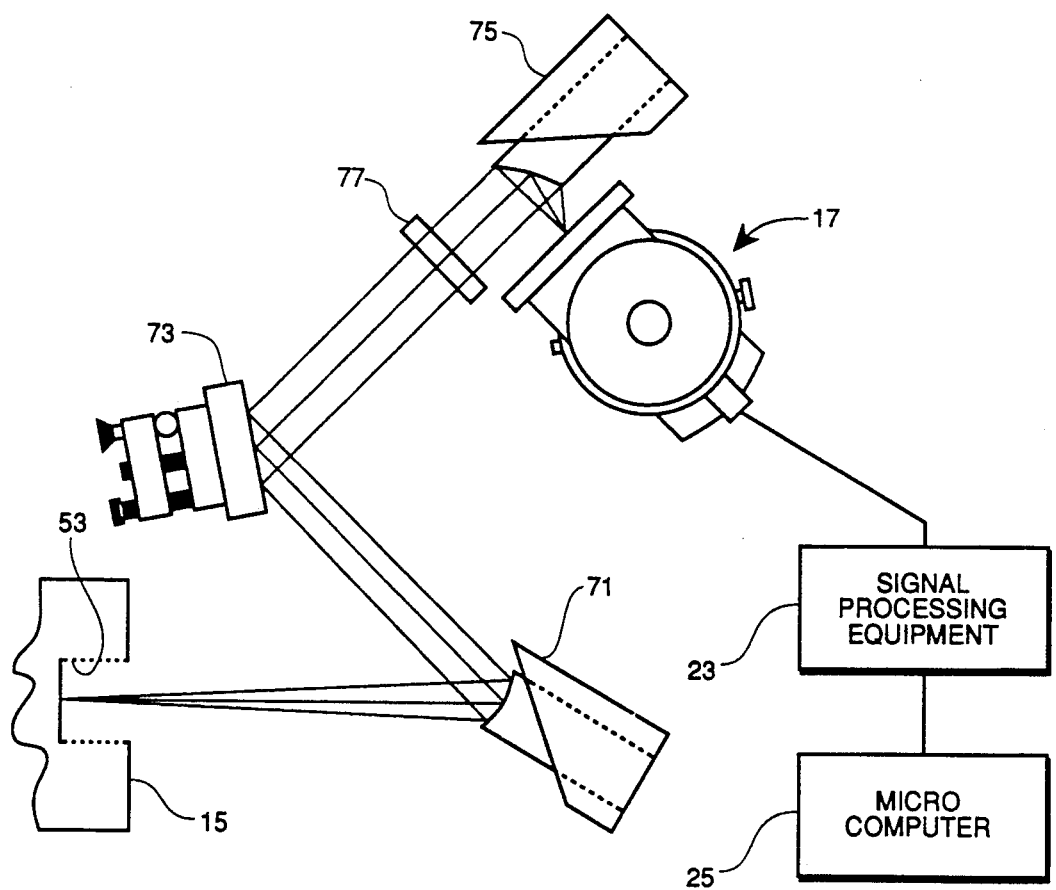
FIG. 4 is an enlarged view of the portion of FIG. 1 depicting the output optics for the spectrometer of FIGS. 1-3.

FIG. 4 shows an enlarged view of a portion of FIG. 1 including spectrometer 15 output optics, detector 17, signal processing electronics 23 and computer 25. Light exiting slit 53 of spectrometer 15 is collected by off-axis parabolic mirror 71 (identical to mirrors 48,49) and folded by flat mirror 73 and relayed to (f/1.5) fast focusing mirror 75. Mirror 75 speed results in a theoretical demagnification of the filament image by a factor of 5, which demagnification is useful in minimizing detector element size and thereby minimizing noise level of detector 17. The element in detector 17 is located at the focal plane of mirror 75. A second mirror identical to mirror 75 may be included to collect light from laser 13. In the demonstration unit, detector 17 was a photodiode detector (Judson model J10D-M204-1) including a liquid nitrogen cooled photovoltaic InSb photoelement having a non-standard 4 mm$^2$ active detector area (sized to match the input optics) covering the full desired 1-5 $\mu$ spectral band. Detector 17 had a detectivity greater than about $10^{11}$ at about 4.0 $\mu$ and about $10^{10}$ at 1.0 $\mu$; responsivity was observed as better than 2.5 A per watt, and quantum efficiency better than 85%. Reduction of noise equivalent power (equals the inverse product of detector detectivity times element area times integration time) in detector 17 is important. Although theoretical curves provided by the manufacturer of detector 17 suggest that equivalent noise levels as low as 0.3 pW can be obtained, in practice an equivalent noise level of about 3 $\mu$W was observed; this means that a density measurement of 6 requires 3 $\mu$W to be delivered to detector 17, and a density of 7 requires 30 $\mu$W to be delivered. Minimum measured output voltage of the detector was 0.2 nV, thus a signal level of 580 $\mu$V corresponds to a dynamic range of 64 dB, which range is limited only by the ratio of the maximum light signal that can be delivered to the detector divided by the noise level of densitometer 10. Densitometer 10 operation is therefore optimum at the lowest practical attainable levels of optical, electronic and thermal noise in the source, optics, spectrometer and detector. Accordingly, attention to source 11 stability, exclusion of extraneous light through the use of light baffles and housings (not shown in the figures) along the optics, grounding of the detector, preamplifier and optics table, and other well-known preventive measures may be desirable to enhance performance of densitometer 10. Further, optional bandpass filter 77 may be positioned for maximum throughput in the output optics of spectrometer 15 as close to detector 17 as practical (FIG. 4) to assist in the attenuation of all but the desired wavelength(s).

Detector 17 was shown to be linear to within a few percent over a dynamic range of 6 decades, which conveniently allows density measurements based on signal voltages taken only with respect to sample optics 19. Dynamic range of the system can be extended using suitable laser sources to a level beyond the combined 70 dB dynamic range afforded by attenuators 36–39.

Signal processing electronics 23 may include preamplifier 23a (EG&G Judson mod PA-9) and lock-in amplifier 23b (EG&G Princeton Applied Research mod 5209) operatively connected to computer 25. Detector 17 signals from electronics 23 are synchronized to chopper 35 frequency and input to computer 25 with the wavelength at which measurements are made. In the demonstration unit, computer 25 (Zenith Z-200, 650 K core memory, 40 MB hard drive) controlled diode laser drive frequency, wavelength and output power; controlled wavelength setting and wavelength scanning of spectrometer 15; acquired, digitized and analyzed spectrophotometric measurements; and interpreted, displayed and recorded data.

Mirrors in optics 19,21 are gold plated to minimize losses in the IR, particularly at 1–1.5 $\mu$, but can be replaced with aluminum mirrors for operation in the visible. The f number of optics 19,21,48,49 should match the f number of mirrors 57,59 within spectrometer 15 in order to maximize throughput of the entire system. Each optical element in optics 19,21 included micrometer mounts permitting precision three-dimensional adjustments. The only moving parts in densitometer 10 are the light chopper, variable slits, filter wheels and spectrometer gratings, of which optical alignment is sensitive only to gratings 55,56. Because densitometer 10 may operate at relatively low resolution of spectrometer 15, grating alignment is not a major factor in the reliability of the densitometer.

The invention therefore provides a reliable, high resolution infrared densitometer. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim :

1. A high resolution infrared densitometer system, comprising:
    (a) a light source of broad spectral character;
    (b) optical means for forming first and second images of said light source and for projecting said images as respective first and second light beams along respective parallel first sample and second reference optical axes;
    (c) first and second adjustable optical attenuators disposed along respective said first and second optical axes for selectively balancing the light intensity of each said first and second beams;
    (d) tunable high resolution filter means for rejecting from each respective said first and second beams substantially all radiation except for a selected narrow wavelength range;
    (e) a detector for measuring intensities of the filtered said first and second beams; and
    (f) first and second fixed optical attenuators disposed along respective said first and second optical axes for use in conjunction with said adjustable optical attenuators in selectively attenuating said first and second beams.

2. The system of claim 1 wherein said tunable high resolution filter means comprises a spectrometer.

3. The system of claim 1 wherein said light source comprises a hot filament source of controllable temperature and presenting a spectral output in a wavelength range of from about 0.3 to about 10 microns.

4. The system of claim 1 further comprising a rotatable light chopper disposed along said first and second optical axes for modulating at selective modulation rate said first and second beams.

5. The system of claim 1 wherein said first and second adjustable optical attenuators comprise respective first and second adjustable aperture slits.

6. The system of claim 1 wherein said first and second fixed optical attenuators comprise neutral density filters.

7. The system of claim 6 wherein said neutral density filters comprise gold plated $CaF_2$.

8. The system of claim 1 further comprising an auxiliary light source consisting of one of a laser source, an incandescent source and an arc source, and optical means for projecting an auxiliary light beam from said auxiliary light source along said first sample optical axis.

9. The system of claim 8 wherein said auxiliary light source comprises a laser source of radiation having a wavelength in the spectral range of 3 to 5 microns.

10. A high resolution infrared densitometer system, comprising:
    (a) a first light source consisting of one of a laser source, an incandescent source and an arc source;
    (b) a second incandescent light source of broad spectral character;
    (c) optical means for forming respective first and second images of said first and second light sources and for projecting said images as respective first and second light beams along respective parallel first sample and second reference optical axes;
    (d) first and second adjustable optical attenuators disposed along respective said first and second optical axes for selectively balancing the light intensity of each said first and second beams;
    (e) a rotatable light chopper disposed along said first and second optical axes for modulating at selective modulation rate said first and second beams;
    (f) a tunable high resolution spectrometer for rejecting from each respective said first and second beams substantially all radiation except for a selected narrow wavelength range; and
    (g) a detector for measuring intensities of the filtered said first and second beams.

11. The system of claim 10 wherein said second light source comprises a hot filament source of controllable temperature presenting a spectral output in a wavelength range of from about 0.3 to about 10 microns.

12. The system of claim 10 wherein said first and second adjustable optical attenuators comprise respective first and second adjustable aperture slits, and linear variable differential transducers operatively connected to each of said first and second adjustable aperture slits for control of slit opening thereof.

13. The system of claim 10 further comprising first and second fixed optical attenuators disposed along respective said first and second optical axes for use in conjunction with said adjustable optical attenuators in selectively attenuating said first and second beams.

14. The system of claim 13 wherein said first and second fixed optical attenuators comprise neutral density filters.

15. The system of claim 14 wherein said neutral density filters comprise gold plated $CaF_2$.

16. The system of claim 10 wherein said first light source comprises a laser source of radiation having a wavelength in the spectral range of 3 to 5 microns.

17. A method for measuring the optical density of a sample, comprising the steps of:
  (a) providing a first light source consisting of one of a laser source, an incandescent source and an arc source;
  (b) providing a second incandescent light source of broad spectral character;
  (c) forming first and second images of said first and second light sources and projecting said images as respective first and second light beams along respective parallel first sample and second reference optical axes;
  (d) selectively attenuating said first and second beams to balance the intensities thereof;
  (e) inserting a sample along said first sample axis in said first beam;
  (f) selectively attenuating said second beam to again balance the intensities of said first and second beams;
  (g) filtering from each respective said first and second beams substantially all radiation except for a selected narrow wavelength range; and
  (h) calculating the optical density of said sample from the observed increase in attenuation required to balance the intensities of said first and second beams with said sample inserted.

18. The method of claim 17 wherein the step of filtering from each respective said first and second beams substantially all radiation except for a selected narrow wavelength range is performed using a spectrometer.

19. The method of claim 17 wherein said second light source comprises a hot filament source of controllable temperature and presenting a spectral output in a wavelength range of from about 0.3 to about 10 microns.

20. The method of claim 17 wherein the attenuation of said first and second beams is performed using adjustable aperture slits and linear variable differential transducers operatively connected to said adjustable aperture slits for control of slit opening thereof.

21. The method of claim 19 wherein said first light source comprises a laser source of radiation having a wavelength in the spectral range of 3 to 5 microns.

* * * * *